(12) United States Patent
Wegener et al.

(10) Patent No.: US 11,578,298 B2
(45) Date of Patent: Feb. 14, 2023

(54) DEVICE FOR THE CULTIVATION OF AND RADIATION-INDUCED KILLING OF CELLS AND METHOD FOR ANALYZING A MIGRATION AND/OR HEALING OF A WOUND

(71) Applicants: FRAUNHOFER-GESELLSCHAFT ZUR FÖRDERUNG DER ANGEWANDTEN FORSCHUNG E. V., Munich (DE); UNIVERSITÄT REGENSBURG, Regensburg (DE)

(72) Inventors: Joachim Wegener, Laaber (DE); Carina Schmittlein, Regensburg (DE); Michael Skiba, Regensburg (DE)

(73) Assignees: Universität Regensburg, Regensburg (DE); Fraunhofer-Gesellschaft zur förderung der angewandten Forschung e.V., Munich (DE)

( * ) Notice: Subject to any disclaimer, the term of this patent is extended or adjusted under 35 U.S.C. 154(b) by 209 days.

(21) Appl. No.: 16/762,462

(22) PCT Filed: Nov. 6, 2018

(86) PCT No.: PCT/EP2018/080229
§ 371 (c)(1),
(2) Date: May 7, 2020

(87) PCT Pub. No.: WO2019/091939
PCT Pub. Date: May 16, 2019

(65) Prior Publication Data
US 2021/0371795 A1     Dec. 2, 2021

(30) Foreign Application Priority Data
Nov. 10, 2017 (DE) .......... 10 2017 220 067.7

(51) Int. Cl.
*C12M 1/42* (2006.01)
*C12M 1/12* (2006.01)
(Continued)

(52) U.S. Cl.
CPC .......... *C12M 35/02* (2013.01); *C12M 25/02* (2013.01); *C12M 41/46* (2013.01); *C12M 41/48* (2013.01); *G01N 33/5008* (2013.01)

(58) Field of Classification Search
CPC ...... C12M 35/02; C12M 25/02; C12M 41/46; C12M 41/48; C12M 45/07; G01N 33/5008
See application file for complete search history.

(56) References Cited

U.S. PATENT DOCUMENTS 3,172,828 A * 3/1965 Shepard et al. ....... G03G 17/02
430/84
4,579,837 A * 4/1986 Busch .................... C01B 13/02
502/170
(Continued)

FOREIGN PATENT DOCUMENTS

DE   102008024408 A1   11/2009
DE   102009052673 A1    5/2011
(Continued)

OTHER PUBLICATIONS

Machine Translation of JP 3918889 B2 (Year: 2022).*
(Continued)

*Primary Examiner* — Michael L Hobbs
(74) *Attorney, Agent, or Firm* — Leydig, Voit & Mayer, Ltd.

(57) ABSTRACT

The invention relates to a device designed for the cultivation and radiation-induced killing of living biological cells. The device comprises a flat substrate and a functional layer for creating a wound in biological cells, said functional layer being applied to the flat substrate. The functional layer contains at least one photosensitizer which is designed to convert triplet oxygen into singlet oxygen by the application of electromagnetic radiation. As a result, biological cells on the functional layer can be killed by irradiation of low-intensity electromagnetic radiation. A wound can be introduced into a cell layer at a locally defined point easily, quickly, carefully, and in a flexible and cost-effective manner and thus the healing of the wound can be studied. The invention further relates to uses of the devices and a method for analyzing a migration and/or wound healing behavior of biological cells.

18 Claims, 2 Drawing Sheets

(51) Int. Cl.
*C12M 1/34* (2006.01)
*C12M 1/36* (2006.01)
*G01N 33/50* (2006.01)

(56) References Cited

U.S. PATENT DOCUMENTS

| | | | |
|---|---|---|---|
| 5,479,837 A * | 1/1996 | Kyle | F16P 1/02 |
| | | | 248/231.41 |
| 6,309,818 B1 | 10/2001 | Malinda et al. | |
| 7,332,313 B2 | 2/2008 | Giaever et al. | |
| 8,227,223 B2 | 7/2012 | Giaever et al. | |
| 2002/0182591 A1 | 12/2002 | Giaever et al. | |
| 2010/0190228 A1 | 7/2010 | Giaever et al. | |

FOREIGN PATENT DOCUMENTS

| | | | | |
|---|---|---|---|---|
| DE | 102010052196 A1 | 5/2012 | | |
| JP | 3918889 B2 * | 5/2007 | ................ | C09J 7/02 |
| WO | WO-03102133 A2 * | 12/2003 | ................ | C08J 7/18 |

OTHER PUBLICATIONS

European Patent Office, International Search Report in International Application No. PCT/EP2018/080229 (dated Feb. 28, 2019).
European Patent Office, Written Opinion in International Application No. PCT/EP2018/080229 (dated Feb. 28, 2019).
International Bureau of WIPO, International Preliminary Report on Patentability in International Application No. PCT/EP2018/080229 (dated May 12, 2020).

* cited by examiner

DEVICE FOR THE CULTIVATION OF AND RADIATION-INDUCED KILLING OF CELLS AND METHOD FOR ANALYZING A MIGRATION AND/OR HEALING OF A WOUND

CROSS-REFERENCE TO RELATED APPLICATIONS

This patent application is the U.S. national phase of International Application No. PCT/EP2018/080229, filed on Nov. 6, 2018, which claims the benefit of German Patent Application No. 10 2017 220 067.7, filed Nov. 10, 2017, the disclosures of which are incorporated herein by reference in their entireties for all purposes.

A device is provided that is suitable for cultivating and for a radiation-induced killing of living biological cells. The device includes a flat substrate and a functional layer to wound biological cells which is applied to the flat substrate. The functional layer includes at least one photosensitizer that is suitable to convert triplet oxygen into singlet oxygen by an action of electromagnetic radiation. This has the effect that biological cells on the functional layer can be killed by irradiation of low-intensity electromagnetic radiation. A wound can be inflicted in a cell layer simply, fast, gently, flexibly, and inexpensively at a locally defined point and the wound healing can be studied. Uses of the devices and a method of examining a migration and/or a wound healing of biological cells are presented.

BACKGROUND OF THE INVENTION

The coordinated migration of adherent animal (also human) cells as a group while maintaining intact cell-cell junctions plays a key role in a large number of physiological processes. This process, that is called "collective cell migration", cannot only be observed during development processes such as the new formation of organs in embryogenesis, but also in vascularization, the repair of injured tissue layers, or in the healing of wounds. Migrating cells additionally do not only occur in a healthy organism, but also play a decisive role in the invasion and metastasis of malign tumors. The latter is an example for a deregulated pathological cell migration.

To obtain a better understanding of the underlying molecular mechanisms that control and/or influence the collective cell migration and to discover factors that promote or inhibit the cell migration, experimental test processes are required that permit the speed of the cell migration to be quantitatively determined.

Experiments of this kind are preferably carried out using cultivated cells outside a living organism (in vitro). Potential active pharmaceutical ingredients can thereby be tested for a possible influencing of the cell migration without having to make use of animal experiments.

In vitro methods for analyzing the migration of animal cells are generally based on the principle that a cell-free region is created or obtained on a culture substrate (e.g. a Petri dish).

The substrate is covered with cells around this region. Cell-free regions can be subsequently created in an existing continuous cell layer in that a portion of the cell layer is mechanically, chemically, optically, or electrically removed. A wound is thereby produced in the cell layer, which gave this kind of process the name wound healing process.

Alternatively, provision can also be made through mechanical barriers on the population of the culture substrate that a specific region of the substrate remains inaccessible to the cells and the cells can only settle around this region. A time is now determined in an experiment that the cells require to migrate into the cell-free regions subsequently created by wounding or previously created by barriers. The migration speed is calculated from the time required for this and from the distance covered.

Different kinds of in vitro wound healing processes or in vitro migration processes for animal cells to analyze the collective migration of adherent cells in 2D are known in the prior art. The creation of a cell-free region—also called a wound—in an intact cell layer covering the culture substrate and the subsequent documentation of the collective migration of neighboring cells to close the cell-free region again (wound healing) are common to all the approaches.

The different methods can be divided into mechanical, chemical, electrical, or optical processes by the principles used for the wounding of the cell layer. The documentation of the wound healing accompanying the onset of cell migration predominantly takes place by time-resolved microscopy and a subsequent image analysis. In this respect, an electrochemical migration process represents an exception that is based on an electrical wounding of the cell layer and on an electrochemical observation of the cell migration (see e.g. U.S. Pat. No. 7,332,313 B2).

With mechanical wounds, two procedures can generally be distinguished: first a direct wounding of a continuous cell layer by a mechanical scratching off of the cells and second a blocking of a specific region of the culture surface when cell seeding so that this region initially becomes inaccessible for the cells and a cell-free region is likewise produced in an otherwise continuous cell layer. In the very frequently used method of scratching a portion of the cell layer ("scratch process"), a wound is inflicted with the aid of a sharp object or by removing a PDMS layer that is applied to the culture substrate before the cell seeding and one which cells likewise grow. The cells can migrate into the cell-free wound after the wounding (see e.g. U.S. Pat. No. 6,309,818 B1).

In the methods based on the introduction of a barrier, this barrier is removed at a defined point in time so that the migration of the cells into the free surface becomes possible from this point in time onward. The barriers can e.g. be created by application of cytocompatible materials such as PDMS in the desired form. Liquid barriers such as oils or agarose gels are also possible. It is common to both mechanical method variants that the migrating cells migrate into a cell-free region that is not covered with killed cells. The absence of dead cells or of cell residues in the region of the wound was achieved by scratching off or by blocking the surface. A disadvantage of the mechanical methods can be seen in this point since they only unsatisfactorily model the relationships in the living organism (in vivo) since the migrating cells have to migrate through remaining cell residues in the wound healing in vivo. Mechanical wounding is the most widespread technique, which is due to the simplicity of the performance and the independence from a complex and/or expensive research infrastructure. However, this method leaves a number of demands unsatisfied with respect to reproducibility, wound geometry, and automation capability.

In chemical wounding, cells in a selected region of the cell layer are brought to lysis by a direct, local application of cytotoxic substances. It is known in the prior art that a direct, local application of 1M NaOH solution to a cell layer with a subsequent neutralization allows a cell-free wound surface to be produced. Chemical wounding is less widespread due to the difficult controllability and the poor reproducibility that follows therefrom.

It is a disadvantage of mechanical and chemical wounding that they do not permit any analysis of cell migration into a surface covered by dead cells and extracellular material, i.e. the analysis in mechanical and chemical wounding corresponds less to the actual physiological conditions to be found in vivo.

In electrical wounding, the cells are cultivated on a substrate that is functionalized with thin film electrodes composed of gold. The cells grow on the electrodes and on the adjacent regions. If the cell layer is confluent, the cells on the electrodes are exposed to a lethal voltage or to a lethal current dosage. The cells in the periphery of the electrodes remain uninfluenced. The size of the wound is exactly defined by the size of the electrodes. The wounding takes place contactlessly since the feed of the lethal voltage or of the lethal current dosage takes place under software control. Unlike most other processes, the documentation of the migration of the cells from the periphery is not performed microscopically in electrical wounding, but rather by measurement of the electrode impedance since the impedance of the electrode (at a suitable frequency of the AC current used for the measurement) directly correlates with the degree of coverage of the electrodes so that a microscopic documentation becomes unnecessary (see e.g. U.S. Pat. No. 7,332, 313 B2).

A variant of this method uses electrical voltage pulses to avoid a population of the electrode on cell seeding. The cells anchor on the culture substrate around the electrodes and form a continuous layer, while the electrode is kept free by the electrical pulses. The start signal for the migration of the peripheral cells onto the electrode is given by switching off the pulses. The migration of cells onto the electrode can also be quantitatively analyzed in this case using impedance measurements and a microscopic documentation becomes superfluous (see e.g. U.S. Pat. No. 8,227,223 B2). Electrical wounding is above all advantageous due to the high reproducibility, the automation possibility, the very high parallelization capability (throughput), and the independence from microscopes.

In optical wounding, a high heat energy is locally introduced into a cell layer by a local irradiation of the cell layer by means of an IR laser. The heat locally produced by the laser effects a temperature-induced wounding of the cell layer. This method produces uniform wound surfaces and had already been combined with bright field microscopy and automated for the documentation of the migration of the non-wounded cells. It is a disadvantage of this method that IR lasers are required that have very high radiation intensities to effect the temperature increase in the cells of the cell layer to be wounded. These IR lasers are cost-intensive to purchase. It can furthermore not be prevented by the temperature input that the temperature increase at least partially has an effect on adjacent cells that are directly adjacent to the surface irradiated by the laser. The temperature increase could produce a cell response (e.g. upregulation of heat shock proteins) in these cells that could have a positive or negative effect on the migration of the cells. In other words, the temperature input could falsify the result of the migration process. The purchase costs for an IR laser suitable for laser ablation are furthermore high and make the laser ablation method less economical.

SUMMARY OF THE INVENTION

Starting from this, it was the object of the present invention to provide a device with which wounds can be introduced into a cell layer at locally defined points in a simple, fast, gentle, flexible, and inexpensive manner and with which the wound healing (cell migration) can subsequently be studied under conditions that are as physiological as possible, wherein any influence of factors disrupting the analysis (e.g. a sublethal heat effect on cells next to an irradiation zone) should be avoided.

DETAILED DESCRIPTION OF THE EMBODIMENTS

Figure 1:
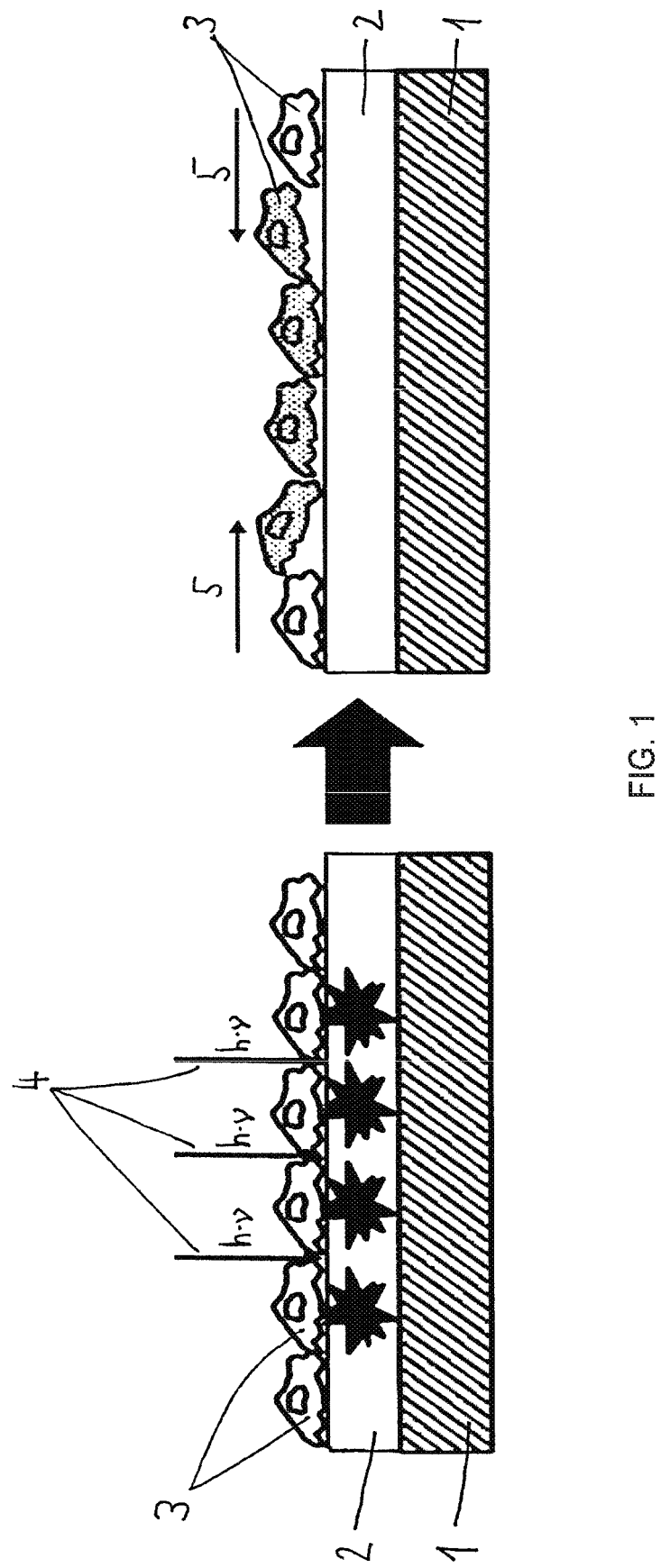
FIG. 1 represents the functional principle of the device in accordance to the invention.

The object is achieved by the features of the device described herein, by the method described herein, and by the advantageous developments thereof. Uses according to the invention are also described.

In accordance with the invention, a device for cultivating and for a radiation-induced killing of living biological cells is provided, comprising
a) a flat substrate; and
b) a functional layer for wounding biological cells applied at least regionally to the flat substrate,
characterized in that the functional layer includes at least one photosensitizer that is suitable to convert triplet oxygen ($^3O_2$) into singlet oxygen ($^1O_2$) by exposure to electromagnetic radiation (preferably at a wavelength in the range of the resonant wavelength of the photosensitizer).

Biological cells can grow on the functional layer for wounding biological cells (i.e. the functional layer is also suitable for cultivating biological cells). A suspension of living biological cells can, for example, be added to the functional layer in a culture medium and can be incubated at 37° C. for the growth. If the functional layer is now irradiated with electromagnetic radiation of a suitable wavelength (e.g. visible light), the photosensitizer in the functional layer converts the triplet oxygen $^3O_2$ present in the environment into singlet oxygen $^1O_2$ that locally kills the biological cells growing on the substrate due to its toxicity. Since the cells grow directly on the functional layer, the distance between the cells and the functional layer is small, but nevertheless sufficient triplet oxygen is present for conversion into the toxic singlet oxygen. It is furthermore ensured that the generated singlet oxygen can reach the living cells at the surface of the functional layer by diffusion.

The device in accordance with the invention makes a mechanical manipulation of the biological cells, which is primarily considered the cause of poor reproducibility, unnecessary for their killing. In the device in accordance with the invention, neither parts of a cell layer nor a previously introduced barrier have to be removed by an experimenter. This independence permits a very cost-efficient and labor-efficient (automated) implementation.

The device in accordance with the invention furthermore has the advantage that singlet oxygen $^1O_2$ has an only very short half life, i.e. it is converted back very quickly into the non-toxic triplet oxygen $^3O_2$. This has the effect that only those cells that were present in direct proximity to the site of creation of the $^1O_2$ are killed. In practice, these are only cells that directly contact the irradiated site of the functional layer. In other words, cell populations or also individual cells can be damaged in a locally very defined manner by the device in accordance with the invention without adjacent cells being affected.

A wound produced with the device in accordance with the invention contains cell components (cell debris) and extracellular matrix components. The migrating cells first have to remove the cell bodies present—analogously to the situation in vivo—before a lateral migration becomes possible. This situation comes very close to the physiological situation in vivo and also much closer than is the case with mechanically or chemically produced wounds since the latter do not have any extracellular matrix or are completely undefined with respect to the extracellular matrix.

The wound production method by irradiation with electromagnetic radiation moreover permits a high precision of wound production and additionally a high flexibility in wound size and wound shape. The similarly precise electrical device and the electrical wounding method are in contrast only adaptable with respect to the wound shape by a change of the electrode shape, which is much more complex and/or expensive, on the one hand, and which considerably restricts the accessible wound geometries, on the other hand.

A further advantage of the device in accordance with the invention is that the excitation of the photosensitizer for the conversion of $^3O_2$ into $^1O_2$ already occurs at low radiation intensities. In brief, the energy input required for this purpose is considerably lower than, for example, the energy input that is necessary in laser ablation of biological cells by an IR laser.

In fact, with the device in accordance with the invention, a simple, optical microscope is already sufficient for the locally selective killing of the cells.

Since the device in accordance with the invention manages without expensive IR lasers, it allows the user a simple and inexpensive analysis of the cell migration and/or wound healing. The analysis can, for example, already be carried out with the aid of the standard equipment of a laboratory working in cell biology (e.g. with a simple fluorescence microscope).

Since no IR lasers have to be used for the killing of the cells, the analysis of the cell migration and/or wound healing is moreover less susceptible to disruption factors caused by IR radiation. It is in particular avoided by the device in accordance with the invention that the heat development in the irradiated region spreads to the adjacent, non-irradiated region and influences the cells present there. Such an influence can be a change in the transcriptome and/or proteome of the adjacent living cells (e.g. an increased production of heat shock proteins), which can have an (unwanted) influence on the cell migration or on the effect of migration-changing substances. Such an influence is avoided by the device in accordance with the invention.

The device can be characterized in that the flat substrate comprises or consists of a material that is selected from the group consisting of glass, plastic, and combinations thereof, with the material preferably being selected from the group consisting of ceramics, metal, semiconductors, glass, polycarbonate, polystyrene, PMMA, PEN, polyester, and combinations thereof. The flat substrate preferably has a round or angular geometry.

The flat surface preferably has a hydrophilic surface since this improves the adhesion of biological cells. The substrate is particularly preferably sterilized and/or hydrophilized by plasma treatment. An advantage is an improved suitability for the culture of different adherent biological cells.

In a preferred embodiment, the flat substrate is transparent for electromagnetic radiation at a wavelength in a range selected from the group of UV range, VIS range, IR range, and combinations thereof, preferably in the VIS range. This embodiment is advantageous since it permits an irradiation of the electromagnetic radiation from a side remote from the functional layer (and the living cells) (e.g. from "below" onto the device). This makes it possible to define the damage site even more precisely since an absorption and/or scattering of the irradiated electromagnetic radiation by the biological cells and/or by culture medium or buffer medium can be precluded.

Alternatively, the flat substrate can be nontransparent for electromagnetic radiation at a wavelength in a range selected from the group of UV range, VIS range, IR range, and combinations thereof, preferably in the VIS range.

The flat substrate can have one or more walls remote from the functional layer. These walls can form one or more wells on the flat substrate. The wall(s) can be monolithic with the flat substrate or can be connected to the flat substrate in a fluid-tight manner. The connection can be with material continuity, with a force fit, and/or with shape matching. It is in particular advantageous for the flat substrate to form a 6-well plate, a 12-well plate, a 24-well plate, or a 96-well plate with the walls. The more wells the plate has, the more individual examination of the migration and/or wound healing of biological cells can be carried out at the same time. A high throughput is in particular a decisive advantage on a testing of an influence of different active ingredients on the migration of the cells.

The functional layer can comprise or consist of a material that is selected from the group consisting of an oxygen-permeable polymer (e.g. a polymeric plastic), wherein the material is preferably selected from the group consisting of polystyrene, PMMA, PEDOT, PDMS, and combinations thereof, with the material particularly preferably being polystyrene.

The functional layer preferably has a hydrophilic surface since this assists the adhesion of biological cells. The functional layer is particularly preferably sterilized and/or hydrophilized by plasma treatment. An advantage here is an improved suitability for the culture of different adherent biological cells.

In a preferred embodiment, the functional layer is transparent for electromagnetic radiation at a wavelength in a range selected from the group of UV range, VIS range, IR range, and combinations thereof, preferably in the VIS range. This embodiment is advantageous since on an irradiation of the electromagnetic radiation from a side remote from the living cells (e.g. from "below" onto the functional layer), the electromagnetic radiation at high intensity reaches the side of the functional layer that faces the living cells. This makes it possible to implement the killing of the biological cells at a lower radiation intensity.

If both the substrate and the functional layer are transparent for visible light, the advantage moreover results that the cells cultivated on the surface of the substrate can be examined with the aid of a microscope having an inverse optic and that the cell migration after the wounding can also hereby be documented. In combination with an automated microscope, a completely automated analysis of a migration and/or wound healing of biological cells is furthermore possible, which decisively increases the throughput of such examinations. In the case of a microscope as a radiation source, the size and shape of the wound can be set very flexibly in dependence on the cell type via the illumination parameters and via the travel distance of the microscope optics (adaptation of the irradiation surface). The wound size can furthermore be finely adjusted by the optics used (lens magnification and/or filters used).

The functional layer can have a thickness in the range from 1 to 100 µm, preferably 2 to 60 µm, particularly preferably 3 to 40 µm, very particularly preferably 4 to 20 µm, in particular 5 to 10 µm. The thinner the functional layer, the less photosensitizer has to be used. Since photosensitizers can be very expensive (e.g. platinum(II)-5,10,15,20-tetrakis(2,3,4,5,6-pentafluorophenyl)-porphyrin), a functional layer having a thickness in this range means that the device in accordance with the invention can be provided more economically without any functional loss.

The functional layer can be producible or produced using a coating process that is preferably selected from the group consisting of spin coating, doctor blade coating, spray coating, and combinations thereof. The thickness of the functional layer can be regulated, for example, by the rotational speed in the spin coating, with the functional layer comprising a polymer matrix (oxygen permeable) into which the photosensitizer is embedded after a complete evaporation of the solvent. A mixture of polymer and photosensitizer can, for example, be applied to different flat substrates with the aid of the spin coating process so that the coating of areas of different sizes is possible with the functional layer.

In a preferred embodiment, the at least one photosensitizer is suitable to absorb electromagnetic radiation at a wavelength in a range selected from the group of UV range, VIS range, IR range, and combinations thereof, preferably at a wavelength in the VIS range, with the at least one photosensitizer preferably being selected from the group consisting of molecules that are suitable to effect an energy transfer from the triplet energy state of oxygen to the singlet energy state of oxygen by means of electromagnetic radiation. The at least one photosensitizer is particularly preferably selected from the group consisting of luminophores that are suitable for phosphorescence. The photosensitizer is very particularly preferably selected from the group consisting of photosensitizers having at least a porphyrin structure, photosensitizers having at least a naphthalene structure, photosensitizers having at least a triphenylmethane structure, and combinations thereof, with the at least one photosensitizer in particular comprising and/or consisting of platinum(II)-5,10,15,20-tetrakis(2,3,4,5,6-pentafluorophenyl)-porphyrin, eosin, rose bengal, naphthalene, and/or benzophenone.

In accordance with the invention, a method for examining a migration and/or wound healing of biological cells is further provided, comprising the steps
a) Exposing a partial region of a layer of living biological cells which are located on a functional layer for wounding biological cells of a device in accordance with one of the preceding claims to electromagnetic radiation from an irradiation source so that the biological cells in the partial region die; and
b) Examining a migration of living biological cells from outside the partial region into the partial region.

The observation of the migration of the living biological cells from outside the partial region into the partial region advantageously takes place when the action of electromagnetic radiation has been stopped or has at least been reduced to an intensity at which biological cells do not die (any more) in at least one region (marginal region) of the partial region.

The electromagnetic radiation used in the method can
i) have one or more wavelengths that fall in a range selected from the group of UV range, VIS range, IR range, and combinations thereof, preferably VIS range, particularly preferably in a range of the resonant wavelength of the photosensitizer; and/or
ii) have a power in the range from 1 mW to 1 W; and/or
iii) act on the partial region for a time period of 1 sec to 60 sec; and/or
iv) be produced by at least one radiation source selected from the group consisting of laser, one or more LEDs, mercury vapor lamp, metal halide lamp and combinations thereof, optionally together with an optical filter.

The living biological cells can be selected from the group consisting of animal cells, plant cells, microorganisms, and mixtures thereof, with the living biological cells preferably being selected from the group consisting of animal cells (e.g. at least one animal tissue), particularly preferably from the group consisting of animal cancer cells, cardiomyocytes, neuronal cells, liver cells, kidney cells, stem cells, epithelial cells, endothelial cells, and combinations thereof.

In a preferred embodiment, a mask is arranged between the irradiation source and the functional layer having the living cells, said mask allowing the electromagnetic radiation to pass within the partial region and absorbing and/or reflecting it outside the partial region. The use of a mask is in particular of advantage when the flat substrate has a plurality of wells (e.g. 96 wells) since then a killing of the biological cells can take place simultaneously on a defined surface via a suitable mask via only one single illumination in each of the wells. Each of the wells (e.g. 96 units) therefore does not have to be traveled to individually by a laser, for example. The time advantage associated with the use of the mask increases proportionally with the number of wells and above all makes high throughput analyses more economical.

After the action of electromagnetic radiation, the partial region of the layer of dead biological cells can be bounded by a margin which abuts the living biological cells on at least 20%, preferably at least 40%, particularly preferably at least 60%, very particularly preferably at least 80%, in particular 100%, of its length.

In a preferred embodiment, the examination of a migration of biological cells comprises
i) the addition of a substance to the living cells which is presumed to have a migration-promoting or migration-inhibiting influence on the living biological cells; and/or
ii) the determination of a speed at which the living biological cells migrate into the partial region; and/or
iii) the determination of a time until the complete partial region is covered by living biological cells; and/or
iv) a comparative characterization of different cell types, preferably a comparison between healthy cells and cancer cells, a comparison of cancer cells having different metastatic potentials, a comparison between epithelial cells from different organs, and/or a comparison of different immune cells, optionally in the presence of at least one added active ingredient or without any addition of an active ingredient.

The use of the device in accordance with the invention is furthermore proposed for examining a migration and/or a wound healing of biological cells, preferably for discovering chemical substances (active agents) that influence the migration of biological cells in wound healing, particularly preferably for discovering active agents that inhibit the migration of cancer cells, and/or for discovering active agents that modulate the migration of immunocompetent cells.

The subject matter in accordance with the invention will be explained in more detail with reference to the following Figures without intending to restrict it to the specific embodiments shown here.

FIG. 1 represents the functional principle of the device in accordance with the invention. The functional layer 2 that includes at least one photosensitizer is applied to the flat substrate 1 of the device. Living biological cells 3 are irradiated with electromagnetic radiation 4 in a locally bounded manner. The locally bounded illumination by light matching the absorption band of the photosensitizer results in the locally bounded production of singlet oxygen $^1O_2$ that is toxic, but of short range. This short-range singlet oxygen is toxic to cells and effects a locally very defined dying of the biological cells 3 present on the functional layer 2, whereby a free space arises on the functional layer 2. It can be observed after the irradiation that the living biological cells migrate into the created free space on the functional layer (see migration direction arrow 5).

Figure 2:
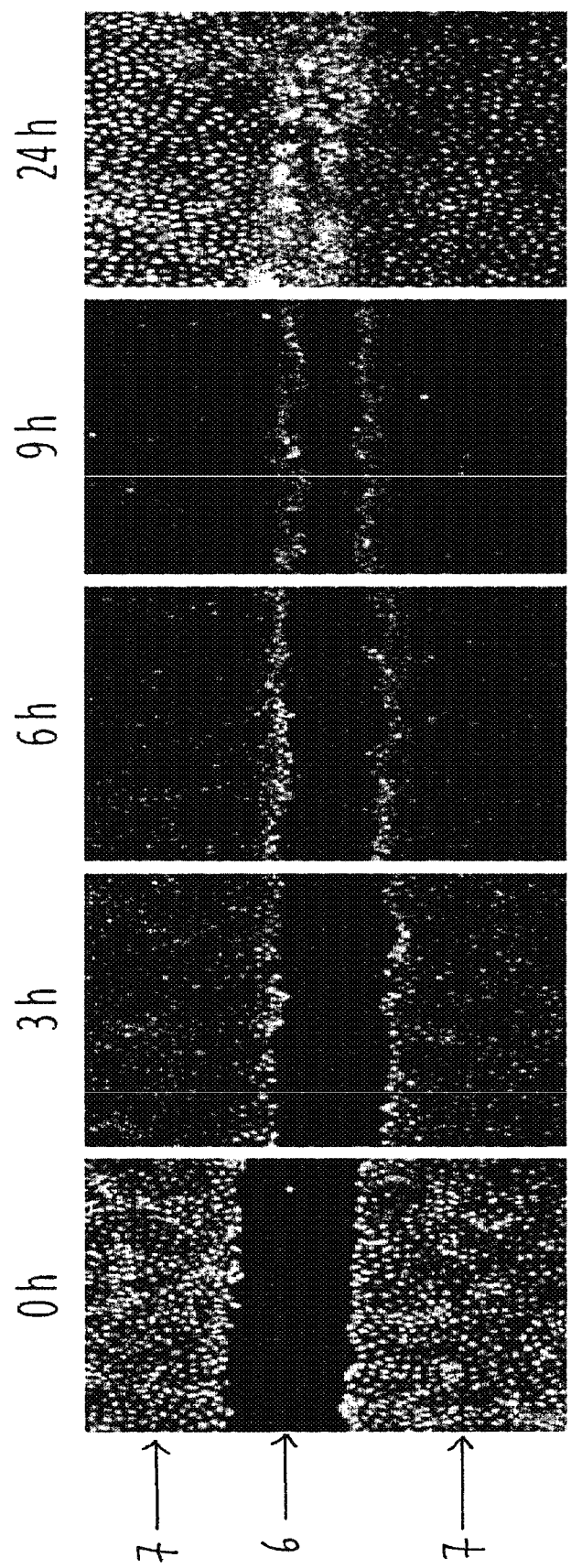
FIG. 2 shows the functionality of the device in accordance with the invention with reference to a fluorescence microscope image series.

FIG. 2 shows the functionality of the device in accordance with the invention with reference to a fluorescence microscope image series. A confluent cell layer was first cultivated on the functional layer of a device in accordance with the invention. The cells along an almost horizontal strip in the cell layer were killed by the direct and locally selective release of $^1O_2$ by irradiation with laser light of a suitable wavelength, focused through the 10× lens of a fluorescence microscope, whereby a partial region 6 of the functional layer is produced that has dead cells. The cells were subsequently subjected to an established live/dead dyeing.

The functional test documents by the live/dead contrast the introduction of an almost horizontal wound (see partial region 6 of the functional layer with dead cells) into an otherwise continuous cell layer (see partial region 7 of the functional layer with living cells). As the time passes, the cells migrate from the periphery 7 into the newly created wound 6, replace the still present dead cells, and close the wound. The record at 0 h shows the cell layer directly after the irradiation with a VIS laser along a horizontal strip. The cell layer is likewise shown after 3 hours, six hours, nine hours, and 24 hours regeneration time.

REFERENCE NUMERAL LIST

1: flat substrate
2: functional layer
3: biological cells
4: electromagnetic radiation
5: cell migration direction
6: partial region of the functional layer having dead cells
7: partial region of the functional layer having living cells

The invention claimed is:

1. A device for cultivating and for radiation-induced killing of living biological cells, comprising
   (a) a flat substrate; and
   (b) a functional layer for wounding biological cells applied at least regionally to the flat substrate,
   wherein the functional layer includes at least one photosensitizer that is suitable to convert triplet oxygen into singlet oxygen by exposure to electromagnetic radiation, and the functional layer has a thickness in the range from 1 to 100 μm.

2. The device in accordance with claim 1, wherein the flat substrate comprises a material selected from the group consisting of glass, plastic, and combinations thereof.

3. The device in accordance with claim 1, wherein the flat substrate
   (i) is transparent for electromagnetic radiation at a wavelength in a range selected from the group of UV range, VIS range, IR range, and combinations thereof, or
   (ii) is nontransparent for electromagnetic radiation at a wavelength in a range selected from the group of UV range, VIS range, IR range, and combinations thereof.

4. The device in accordance with claim 1, wherein the functional layer comprises a material selected from the group consisting of an oxygen permeable polymer.

5. The device in accordance with claim 1, wherein the functional layer is transparent for electromagnetic radiation at a wavelength in a range selected from the group of UV range, VIS range, IR range, and combinations thereof.

6. The device in accordance with claim 1, wherein the functional layer is produced by a coating process.

7. The device in accordance with claim 1, wherein the at least one photosensitizer is suitable to absorb electromagnetic radiation at a wavelength in a range selected from the group of UV range, VIS range, IR range, and combinations thereof.

8. The device in accordance with claim 7, wherein the at least one photosensitizer is suitable to absorb electromagnetic radiation at a wavelength in the VIS range.

9. The device in accordance with claim 8, wherein the at least one photosensitizer is selected from the group consisting of molecules that are suitable to effect an energy transfer from the triplet energy state of oxygen to the singlet energy state of oxygen by electromagnetic radiation.

10. The device in accordance with claim 9, wherein the at least one photosensitizer is selected from the group consisting of luminophores that are suitable for phosphorescence.

11. The device in accordance with claim 9, wherein the at least one photosensitizer is selected from the group consisting of photosensitizers having at least a porphyrin structure, photosensitizers having at least a naphthalene structure, photosensitizers having at least a triphenylmethane structure, and combinations thereof.

12. The device in accordance with claim 9, wherein at least one photosensitizer comprises platinum(II)-5,10,15,20-tetrakis(2,3,4,5,6-pentafluorophenyl)-porphyrin, eosin, rose bengal, naphthalene, and/or benzophenone.

13. A method of examining migration and/or wound healing of biological cells, comprising:
   (a) exposing a partial region of a layer of living biological cells which are located on a functional layer for wounding biological cells of a device in accordance with claim 1 to electromagnetic radiation from an irradiation source so that the biological cells in the partial region die; and
   (b) examining a migration of living biological cells from outside the partial region into the partial region.

14. The method in accordance with claim 13, wherein the electromagnetic radiation
   (i) has one or more wavelengths that fall in a range selected from the group of UV range, VIS range, IR range, and combinations thereof; and/or
   (ii) has a power in the range from 1 mW to 1 W; and/or
   (iii) acts on the partial region for a time period of 1 sec to 60 sec.; and/or
   (iii) is produced by at least one radiation source selected from the group consisting of laser, one or more LEDs, mercury vapor lamp, metal halide lamp and combinations thereof, optionally together with an optical filter.

15. The method in accordance with claim 13, wherein the living biological cells are selected from the group consisting of animal cells, plant cells, microorganisms, and mixtures thereof.

16. The method in accordance with claim 13, wherein a mask is arranged between the irradiation source and the functional layer having the living cells, said mask allowing the electromagnetic radiation to pass within the partial region and absorbing and/or reflecting it outside the partial region.

17. The method in accordance claim 13, wherein after the action of electromagnetic radiation, the partial region of the layer of dead biological cells is bounded by a margin which abuts the living biological cells on at least 20% of its length.

18. The method in accordance with claim 13, wherein the examination of a migration of biological cells comprises,
   (i) the addition of a substance, which has a migration-promoting or migration-inhibiting influence on the living biological cells, to the living cells; and/or
   (ii) the determination of a speed at which the living biological cells migrate into the partial region; and/or
   (ii) the determination of a time until the complete partial region is covered by living biological cells; and/or
   (iv) a comparative characterization of different cell types, optionally in the presence of at least one added active agent or without any addition of an active agent.

\* \* \* \* \*